(12) United States Patent
Beyar et al.

(10) Patent No.: US 8,399,871 B2
(45) Date of Patent: Mar. 19, 2013

(54) PROTECTED CONTROL CONSOLE APPARATUSES

(75) Inventors: Rafael Beyar, Haifa (IL); Tal Wenderow, West Newton, MA (US); Moshe DePaz, Boston, MA (US)

(73) Assignee: Corindus Inc., Natick, MA (US)

( * ) Notice: Subject to any disclaimer, the term of this patent is extended or adjusted under 35 U.S.C. 154(b) by 241 days.

(21) Appl. No.: 11/715,876

(22) Filed: Mar. 9, 2007

(65) Prior Publication Data
US 2008/0217564 A1    Sep. 11, 2008

(51) Int. Cl.
*G21F 3/00* (2006.01)
(52) U.S. Cl. .................. 250/515.1; 250/505.1; 604/510; 604/528; 600/106; 600/114; 600/137; 378/65
(58) Field of Classification Search ............... 250/515.1, 250/491.1, 493.1, 496.1, 497.1, 498.1, 503.1, 250/505.1, 517.1; 604/510, 528; 600/106, 600/114, 137; 378/65
See application file for complete search history.

(56) References Cited

U.S. PATENT DOCUMENTS

| | | | | |
|---|---|---|---|---|
| 2,718,598 A * | 9/1955 | Graf | ............................ | 250/515.1 |
| 3,147,953 A * | 9/1964 | Arth | ............................ | 254/10 C |
| 3,308,297 A * | 3/1967 | Mansker | .................... | 250/515.1 |
| 4,254,341 A * | 3/1981 | Herr et al. | .................. | 250/519.1 |
| 4,581,538 A * | 4/1986 | Lenhart | ....................... | 250/519.1 |
| 4,965,456 A * | 10/1990 | Huettenrauch et al. | .... | 250/515.1 |
| 4,977,588 A * | 12/1990 | Van der Ende | ............... | 378/196 |
| 5,090,044 A * | 2/1992 | Kobayashi | .................... | 378/145 |
| 5,185,778 A * | 2/1993 | Magram | ........................ | 378/196 |
| 5,584,078 A * | 12/1996 | Saboory | ............................ | 2/427 |
| 5,697,377 A | 12/1997 | Wittkampf | | |
| 5,842,987 A * | 12/1998 | Sahadevan | ..................... | 600/407 |
| 5,851,182 A * | 12/1998 | Sahadevan | ..................... | 600/407 |
| 5,981,964 A * | 11/1999 | McAuley et al. | .......... | 250/515.1 |
| 6,448,571 B1 | 9/2002 | Goldstein | | |
| 6,499,163 B1 * | 12/2002 | Stensby | ............................ | 5/618 |
| 6,554,472 B1 * | 4/2003 | Dietz et al. | ..................... | 378/197 |
| 6,653,648 B2 | 11/2003 | Goldstein | | |
| 6,726,675 B1 * | 4/2004 | Beyar | ............................ | 604/510 |
| 7,112,811 B2 * | 9/2006 | Lemer | ......................... | 250/515.1 |
| 7,608,847 B2 * | 10/2009 | Rees | ........................... | 250/516.1 |
| 2002/0109107 A1 * | 8/2002 | Goldstein | .................. | 250/505.1 |

(Continued)

FOREIGN PATENT DOCUMENTS

FR 2167098 A5 * 12/1971
WO WO 2007/036925  4/2007

OTHER PUBLICATIONS

International Preliminary Report on Patentability Dated Oct. 18, 2007 From the International Preliminary Examining Authority Re.: Application No. PCT/IL05/01054.
Written Opinion Dated Jul. 9, 2007 From the International Preliminary Examining Authority Re.: Application No. PCT/IL05/01054.

*Primary Examiner* — Michael Logie
(74) *Attorney, Agent, or Firm* — Rathe Lindenbaum LLP (57) ABSTRACT

An apparatus for control of a procedure, comprising: a communications interface; a control console, wherein the control console is adapted to provide control commands via the communications interface to at least one of: at least one imaging device or at least one medical instrument used to perform the procedure; and, at least one radiation shield attached to the control console and positioned between the control console and a patient on which the procedure is being performed, wherein the apparatus is separately movable from at least one of the at least one imaging device, the patient or the at least one medical instrument.

35 Claims, 5 Drawing Sheets

U.S. PATENT DOCUMENTS

| | | | |
|---|---|---|---|
| 2002/0177789 A1* | 11/2002 | Ferry et al. | 600/585 |
| 2003/0078003 A1* | 4/2003 | Hunter et al. | 455/41 |
| 2004/0113498 A1* | 6/2004 | Kroenke | 307/115 |
| 2009/0110152 A1* | 4/2009 | Manzke et al. | 378/195 |

* cited by examiner

PROTECTED CONTROL CONSOLE APPARATUSES

RELATED APPLICATIONS

This Application is related to PCT Application No. PCT/IL2005/001054, filed on Sep. 29, 2005, entitled "Methods and Apparatuses for Treatment of Hollow Organs", the disclosure of which is incorporated herein by reference.

FIELD OF THE INVENTION

The present invention relates to protected control console apparatuses and method for using same. For example, radiation protection is provided in combination with a control console used for performing procedures on a patient, in some embodiments of the invention.

BACKGROUND OF THE INVENTION

Today, a wide variety of medical procedures are performed on patients which require the assistance of imaging and other devices which expose medical professionals to harmful substances, for example radiation. Typically, solutions for providing radiation protection have involved separating the medical professional from the patient and/or providing radiation shielding to the medical professional in the form of bulky radiation shields and/or heavy radiation protective clothing, which themselves have potentially negative ramifications such as operator fatigue, operator neck and back pain and Interventionalists' Disc Disease.

For example, U.S. Pat. No. 6,653,648 and U.S. Application Publication No. 2002/0109107, the disclosures of which are herein incorporated by reference, describe radiation protection systems comprising a radiation resistant cubicle, radiation-shielding screen disposed between a patient and medical professionals within the cubicle, a radiation-shielding flexible interface and an integrated procedural environment which may include a control module, monitor displays, conduit for physiological monitoring or equipment leads, staging platforms, intravenous equipment and an improved radiation-resistant surgical drape.

U.S. Pat. No. 6,448,571, the disclosure of which is herein incorporated by reference, describes a radiation protection system around a patient on an x-ray table including a radiation protection wall with an opening around the x-ray table, a radiation screen over the patient, and a flexible interface joining the cubicle and the x-ray table. The wall shields medical personnel in an operating region from most radiation output by an x-ray emitter. The radiation screen is attached to the x-ray table such that it can be retracted to the foot of the x-ray table and extended over the patient wherein it is interposed between the patient and the medical personnel. The interface has flexible joints attached to the wall and a flexible radiation-resistant skirt that joins the wall to the screen and covers the opening in the wall. An access port may be formed in the screen, and a shielding cloak can cover the access port to surround medical instruments that are threaded through the port and inserted into the patient.

SUMMARY OF THE INVENTION

An aspect of some embodiments of the invention relates to providing a remote control console assembly, with integrated radiation protection, for controlling a medical procedure and/or instruments related to the procedure. In some embodiments of the invention, no radiation protection besides the remote control console assembly is necessary to protect an attending medical professional from harmful radiation. In some embodiments of the invention, the control console assembly is adapted to be mobile, for example being provided with wheels. Optionally, the control console assembly is provided with a window to allow a line of sight between an attending medical professional and the patient and/or to provide radiation protection. In some embodiments of the invention, the control console assembly is provided with an independent power supply for supplying power to components of the assembly without requiring an electrical connection.

In some embodiments of the invention, the control console assembly is provided with a control console adapted to permit an attending medical professional to perform medical procedures on a patient without directly contacting the patient and/or remotely. "Remote" or "remotely" as generally used in this application refers to the control console's ability to maneuver independently of the patient, medical imaging devices and/or medical instruments (described in more detail below) used for performing medical procedures. Examples of this remote ability of the control console include: moving the control console to provide a maximum amount of radiation protection to the attending medical professional; moving the control console in order to have better visibility of the patient; moving the control console so that it does not interfere with the operation of medical imaging devices and/or medical instruments; and/or moving the control console from a first location (e.g. a first room) to a second location (e.g. a second room) in order to allow the ability to perform procedures in more than one location using the same control console.

The control console is provided with operative communication to other devices in order to perform the medical procedures, in an embodiment of the invention. Other devices which can be in communication with the control console include medical imaging devices and/or remotely controlled medical instruments. Optionally, remotely controlled medical instruments include at least one of a catheter or an inflatable/deflatable balloon. In some embodiments of the invention, the control console is removably attached to the control console assembly. Optionally, the control console is provided with a detachable control panel which is interchangeable with other control consoles. Alternatively or additionally, differently configured detachable and/or interchangeable control panels are provided for control console wherein the control panels are adapted to interface with different devices and/or are adapted to assist with the performance of different medical procedures.

In some embodiments of the invention, the control console is provided with at least one information display, for example for monitoring information regarding the patient and/or medical devices being used for treatment of the patient. The control console is provided with at least one input device, in an embodiment of the invention. The at least one input device can be, for example, a keyboard, a touch screen, a mouse and/or a joystick. In some embodiments of the invention, the control console is provided with a software-programmed controller for controlling the at least one information display, the at least one input device, communications with other devices, medical imaging devices, remotely controlled medical instruments and/or other nominal operations of the control console. Optionally, the control console is provided with data storage, for example a hard drive, for saving data. In some embodiments of the invention, the power supply described above is provided to the control console rather than or in addition to the control console assembly.

In an embodiment of the invention, the control console assembly is provided with an emergency stop button which halts the medical procedure for example if there is a problem with the patient and/or the devices being used to treat the patient. Optionally, the emergency stop button halts the medical procedure via the controller.

There is thus provided in accordance with an exemplary embodiment of the invention, an apparatus for control of a procedure, comprising:

a communications interface;

a control console, wherein the control console is adapted to provide control commands via the communications interface to at least one of: at least one imaging device or at least one medical instrument used to perform the procedure; and, at least one radiation shield attached to the control console and positioned between the control console and a patient on which the procedure is being performed, wherein the apparatus is separately movable from at least one of the at least one imaging device, the patient or the at least one medical instrument.

In an exemplary embodiment of the invention, the apparatus is adapted for remote control of at least one of the at least one imaging device or the at least one medical instrument. Alternatively or additionally, the apparatus further comprises a radiation protective window adapted to allow a view of the patient when operating the control console.

In an exemplary embodiment of the invention, the control console is removably attached to the apparatus.

In an exemplary embodiment of the invention, the at least one imaging device is an x-ray, a camera, ultrasound, CT or MRI imaging device.

In an exemplary embodiment of the invention, the at least one medical instrument is a guide wire, a catheter, an ablation catheter, an EM mapping catheter, a pacing catheter, or a balloon.

In an exemplary embodiment of the invention, the communications interface is adapted to provide communication between the control console and an information network.

In an exemplary embodiment of the invention, the communications interface is adapted to provide wireless communication from the control console to at least one of: the at least one imaging device or the at least one medical instrument used to perform the procedure or an information network.

In an exemplary embodiment of the invention, the control console is comprised of at least one input device, at least one output device and a controller. Optionally, the at least one input device is a keyboard, a touch screen display, a mouse or a joystick. Alternatively or additionally, the at least one output device is a graphical display or a force feedback device.

In an exemplary embodiment of the invention, the apparatus further comprises a power supply.

In an exemplary embodiment of the invention, the apparatus further comprises an emergency stop button.

There is also provided in accordance with an exemplary embodiment of the invention, a medical device control system for remote control of a medical instrument, comprising:

at least one medical instrument;

a control console assembly including a communications interface providing control commands for the remote control of the medical instrument; the control console further including a shield being positioned between at least a portion of the communications interface and the medical device manipulator, the shield being transparent and formed of a material substantially preventing radiation from being passed therethrough.

In an exemplary embodiment of the invention, the control console assembly is provided with mobility by at least one of at least one wheel or a motorized track. Alternatively or additionally, the at least one medical instrument is part of a bed side unit.

In an exemplary embodiment of the invention, the system comprises panels operatively secured to the control console assembly to prevent radiation from passing therethrough.

Alternatively or additionally, the system comprises an output device adapted to display output from at least one imaging device employing radiation.

There is also provide din accordance with an exemplary embodiment of the invention, a method for the remote control of at least one medical instrument for use in a medical procedure on a patient comprising:

providing at least one remote controlled medical instrument proximate to the patient;

providing a control console assembly having a communication interface for sending signals to the remote controlled medical instrument, the control console assembly including a transparent shield being formed of a material preventing radiation from passing therethrough;

moving the control console assembly from a first position to a second position to allow an operator to view a patient through the shield; and controlling the at least one medical instrument from behind the shield using the control console assembly in order to perform the medical procedure. Optionally, moving comprises positioning the control console assembly in a second location for performing a medical procedure on a second patient. Alternatively or additionally, the method comprises providing a medical image to the control console formed with a radiation source.

BRIEF DESCRIPTION OF THE FIGURES

Non-limiting embodiments of the invention will be described with reference to the following description of exemplary embodiments, in conjunction with the Figures. The Figures are generally not shown to scale and any measurements are only meant to be exemplary and not necessarily limiting. In the Figures, identical structures, elements or parts which appear in more than one Figure are preferably labeled with a same or similar number in all the Figures in which they appear, in which.

DETAILED DESCRIPTION OF EXEMPLARY EMBODIMENTS

Figure 1:
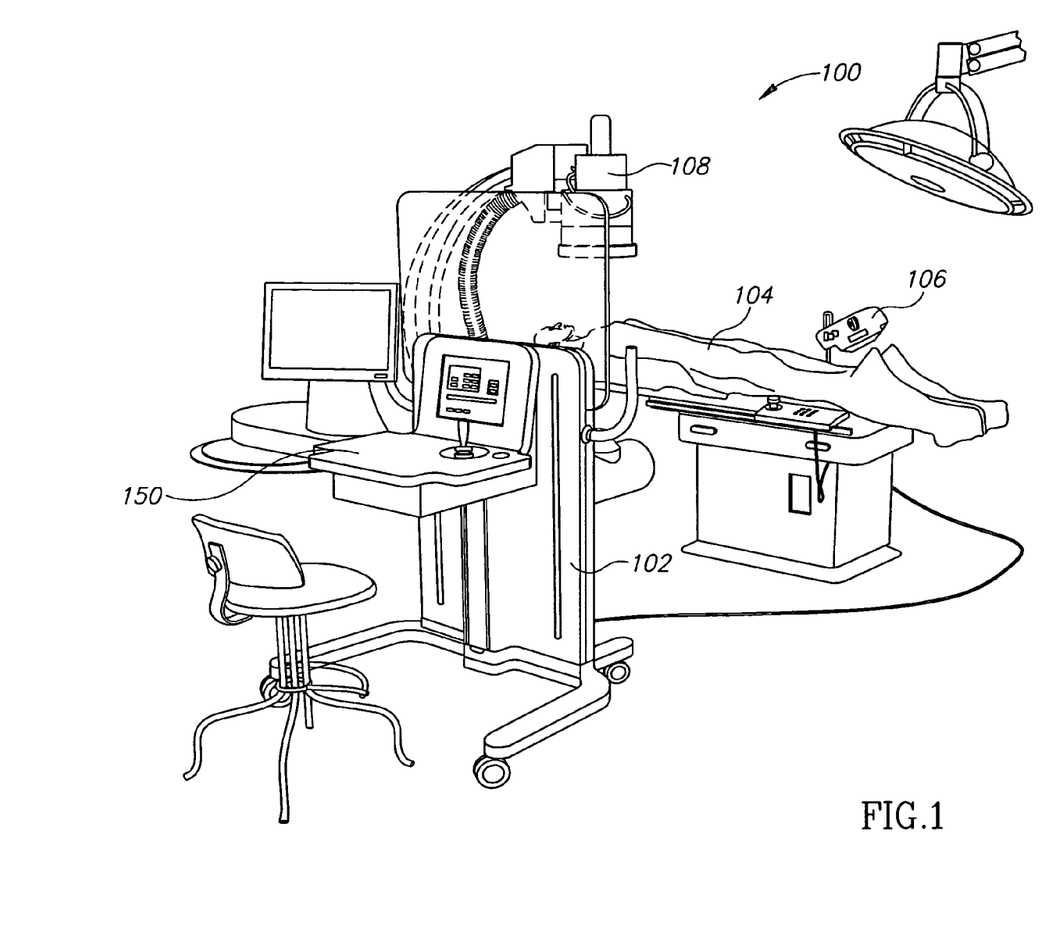
FIG. 1 is an illustration of a medical procedure system including a control console assembly, in accordance with an exemplary embodiment of the invention.

Referring to FIG. 1, a medical procedure system 100 is shown, in accordance with an exemplary embodiment of the invention. A remote control console assembly 102, including a control console 150, is provided to the system 100 for providing command and control to various components of the system 100, in an exemplary embodiment of the invention. Control console assembly 102 is described in more detail below with respect to FIGS. 3-5. Examples of system components include control console 150, a device or devices 106 for performing the medical procedure and a medical imaging device or devices 108 which provide information about a patient 104 in order to assist with the performance of the medical procedure on the patient 104. In an embodiment of the invention, medical imaging device 108 is at least one of an x-ray, a camera, ultrasound, CT or MRI imaging device. Optionally, medical imaging is the medical procedure being performed on the patient, and medical imaging device 108 is the only device being controlled.

In some embodiments of the invention, devices 106 for performing the medical procedure include a bed side unit, which performs some or all or more functions than the catheter propulsion apparatus and the catheter interface of PCT application number PCT/IL2005/001054, as well as assorted medical instruments such as catheters, mapping instruments, pacing instruments, ablative instruments and/or guide wires such as described in PCT/IL2005/001054, U.S. Pat. No. 6,726,675 to Beyar, the disclosure of which is incorporated herein by reference, and/or other medical instruments known in the art.

Also used with the system 100, in an exemplary embodiment of the invention, is at least one medical imaging device 108 such as a fluoroscope, which is used to provide images of the interior of the patient and to show the position of various medical instruments in the patient 104. System 100 can be used with magnetic resonance imaging and/or a computerized tomography scanning device to observe the procedure being performed on the patient 104, in addition to or in place of the fluoroscope. As described above, the fluoroscope (and many other imaging devices) emits potentially harmful radiation which can adversely affect attending medical professionals.

It should be understood that while system components are shown in FIG. 1 in physical proximity to one another, at least one component, such as control console assembly 102 could be located some distance from system 100. Medical procedures can be performed and/or controlled using system 100 in various settings, for example a hospital, a clinic, an outpatient treatment center, a rehabilitation clinic or even a home.

Figure 2:
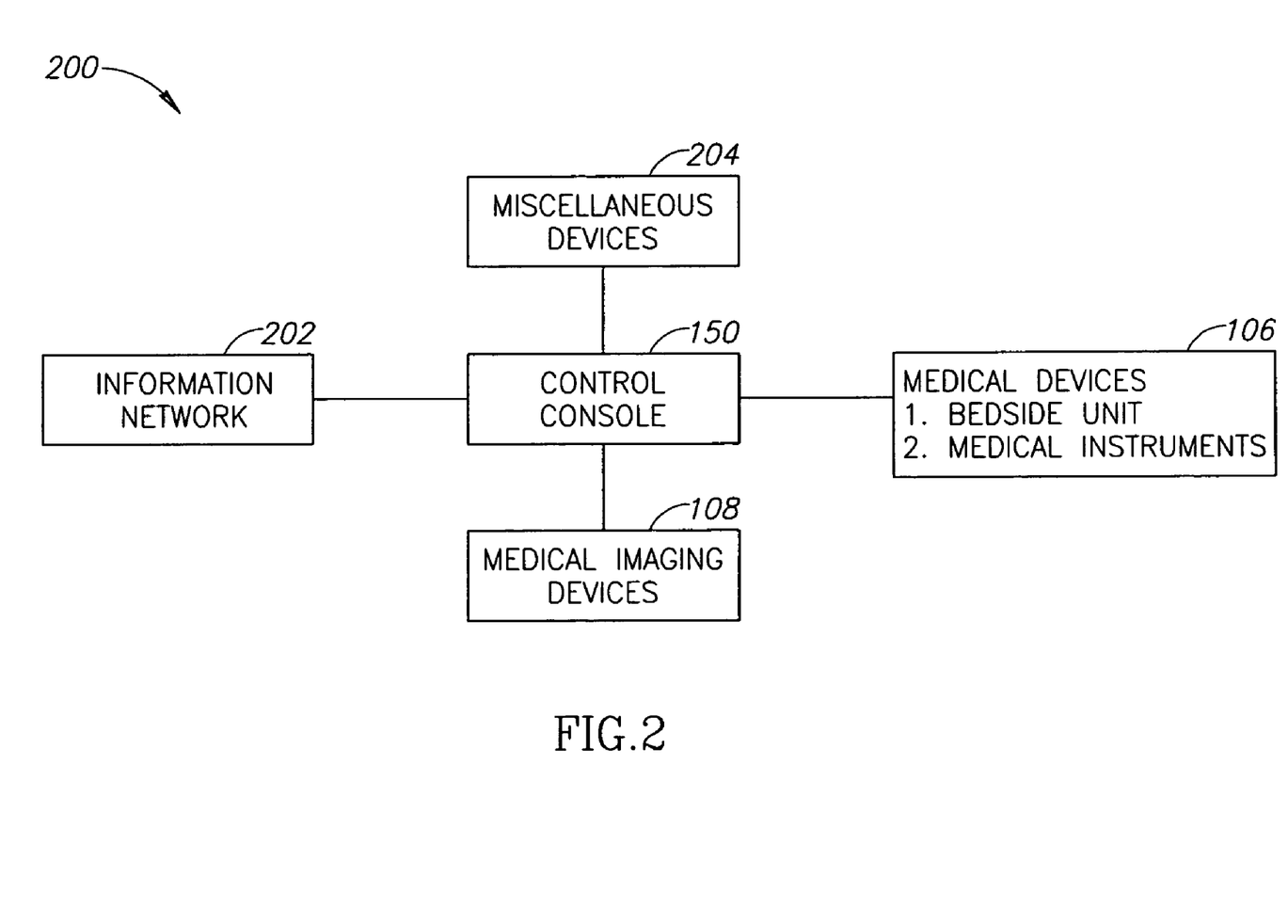
FIG. 2 is a schematic diagram showing operative communication connections between components of the system, in accordance with an exemplary embodiment of the invention.

FIG. 2 is a schematic diagram 200 showing operative communication connections between components of the system 100, in accordance with an exemplary embodiment of the invention. The operative communication connections are used by system 100 to connect control console 150 to other components of system 100, such as devices 106 for performing the medical procedure, medical imaging devices 108, an information network 202 and/or other miscellaneous devices 204. In some embodiments of the invention, the connection is wireless. Optionally, control console 150 is connected using a combination of wired and wireless connections.

In an embodiment of the invention, communication with a plurality of devices 106 for performing the medical procedure is utilized. For example, the bed side unit may contain propulsion mechanisms for extending, retracting and/or rotating medical instruments in the patient 104 which are controlled by control console 150. In some embodiments of the invention, there may also be communication with the instruments themselves, optionally for issuing control commands to the instruments. Examples of control commands communicated to the instruments include activation/deactivation of an ablation catheter, activation/deactivation of sensing in a mapping catheter, activation/deactivation of pacing charges in a pacing catheter, expansion/retraction of an angioplasty-type balloon, and the like.

In some embodiments of the invention, control console 150 is provided with communication to medical imaging devices 108 which are used to image at least a portion of the patient 104 and/or medical instruments being used to perform the medical procedure. In an embodiment of the invention, control console 150 issues control commands to at least one of medical imaging devices 108, for example to help the attending medical professional perform the medical procedure. Exemplary commands include zoom in/out, scaling, positioning, orientation and the like. In some embodiments of the invention, control console 150 is adapted to work with conventional imaging system controls, for example the Innova™ systems offered by GE Healthcare and/or the AXIOM Artis™ family of systems offered by Siemens.

In an embodiment of the invention, information network 202 is the Internet. Optionally, information network 202 is a local network, for example a hospital network. In some embodiments of the invention, information regarding the medical procedure is transmitted over information network 202 to locations outside the operating arena where the procedure is taking place. It should be understood that in some embodiments of the invention, devices 106 for performing the medical procedure, medical imaging devices 108 and/or other miscellaneous devices 204 are directly connected to information network 202 and control console 150 is not an intermediary. Such a configuration would be desirable, for example, if information regarding the medical procedure is to be viewed at a remote location (e.g. for educational or collaborative purposes).

Other miscellaneous devices 204 are optionally controllable from control console 150, in an embodiment of the invention. Examples of miscellaneous devices 204 include ambient lighting controls, ambient temperature controls, operating table adjustment controls, and the like.

Figure 3:
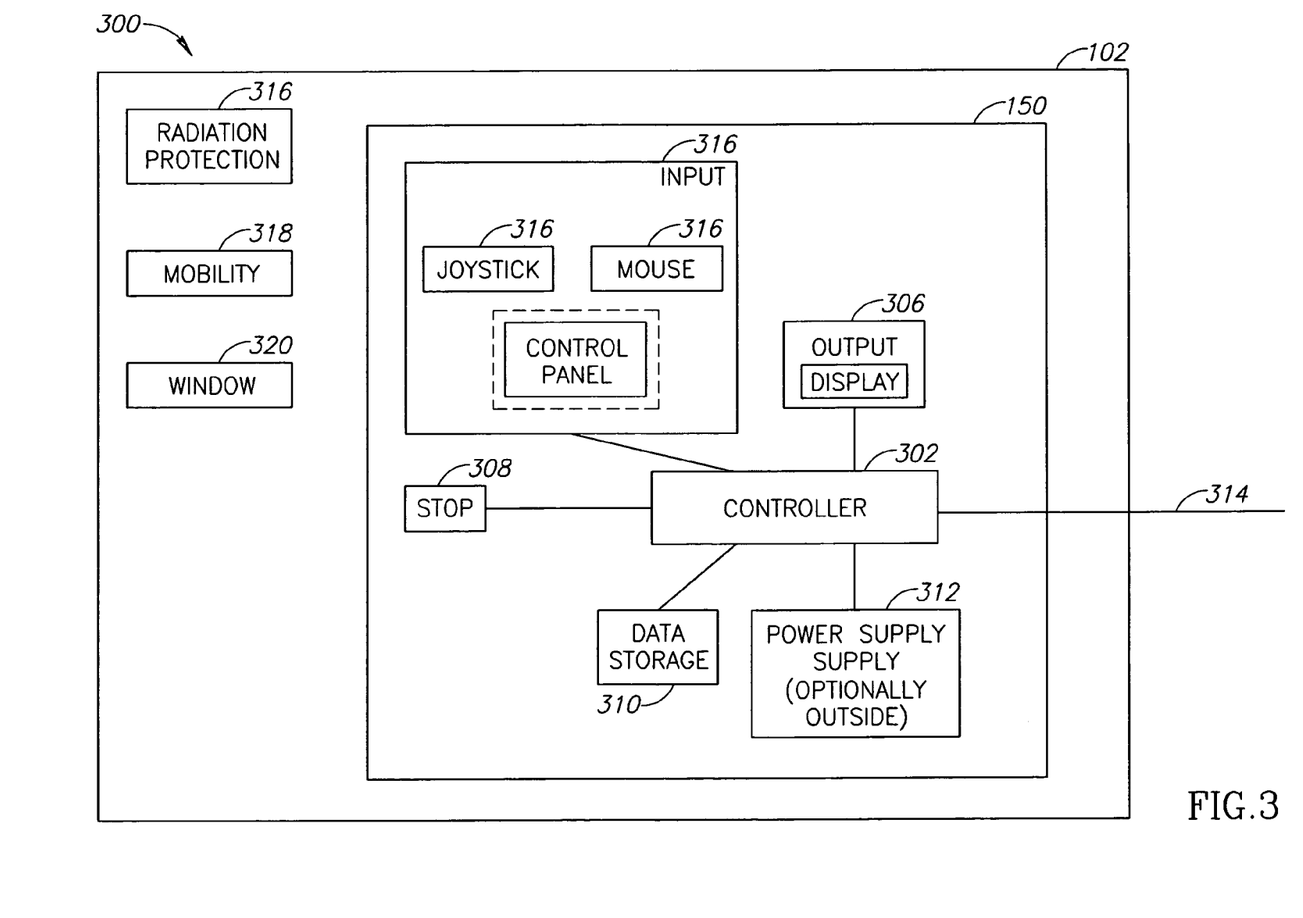
FIG. 3 is a schematic block diagram of the control console assembly, in accordance with an exemplary embodiment of the invention.

Referring to FIG. 3, a schematic block diagram 300 of control console assembly 102 is shown, in accordance with an exemplary embodiment of the invention. Diagram 300 shows a control console 150 configuration, in an exemplary embodiment of the invention. A controller 302 is provided to control console 150 which, in some embodiments of the invention, is used for commanding, controlling receiving commands from and/or coordinating the operation of at least one input device 304, at least one output device 306, an emergency stop 308, and/or a data storage device 310. Control console 150 is also provided with a communication interface 314 for external (i.e. communication outside of control console 150) communication such as described with respect to FIG. 2. As described above, communication interface 314 is optionally wireless. In some embodiments of the invention, control console 150 is a personal computer. In some embodiments of the invention, control console 150 is detachable from control console assembly 102 and/or is interchangeable with other control consoles. Optionally, different control console configurations are adapted to interact with differing suites of equipment and/or to perform different medical procedures. A power supply 312 is provided to control console 150, in some embodiments of the invention. Optionally, power supply 312 is located on control console assembly 102 outside of control console 150. Optionally, power supply 312 is external to control console assembly 102.

In an exemplary embodiment of the invention, at least one input device 304 is used by an attending medical professional to input commands to components of system 100 via control console 150. Examples of at least one input device 304 include: a joystick, a keyboard, a mouse, and/or a touch screen (shown in more detail in FIG. 5). An example of at least one output device 306 includes a graphic display (e.g. LCD, CRT). Optionally, a plurality of output devices 306 is provided to control console 150. In some embodiments of the invention, an input device 304 also functions as an output device 306, for example the joystick and/or the mouse is optionally provided with force feedback and/or the touch screen also functions to provide visual information to the attending medical professional.

In an embodiment of the invention, the touch screen is used for discrete movements of medical instruments (including a guide wire) and the joystick is used for continuous movements of the medical instruments. Optionally, the medical instruments located within the patient can be advanced or retracted in discrete steps of 0.5 mm-1.0 mm using the touch screen. In some embodiments of the invention, discrete medical instrument rotation is performed using control console 150, whereby the medical instrument can be rotated in increments, for example of 30°. In an embodiment of the invention, discrete movements of the medical instrument are performed by touching icons on the touch screen display for the particular movement desired.

Figure 5:
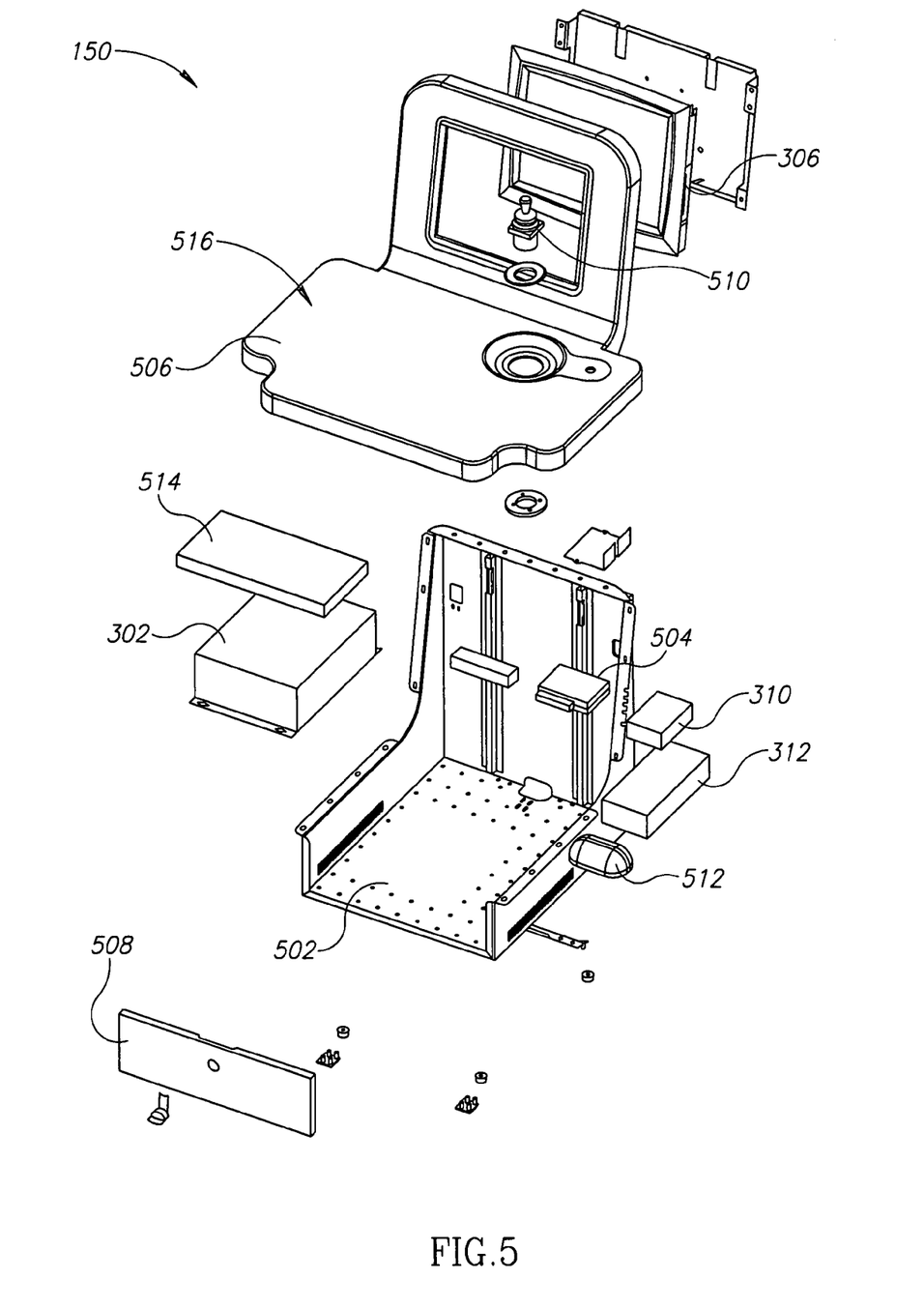

For macro manipulation of a medical instrument, any combination of axial and/or rotational movement can be performed by use of the joystick 510. In some embodiments of the invention, motion of joystick away from and towards the attending medical professional causes linear movement of a medical instrument and movement to the left and right cause rotation. Optionally, rotational movement of joystick 510 about its vertical axis translates to rotational movement of a medical instrument. Optionally, movement to the left or right and/or up or down and/or rotation about the joystick's vertical axis is customizable by the attending medical professional via controller 302 to cause customized movement of a medical instrument, for example using rotation of joystick to cause linear motion. In some embodiments of the invention, controller 302 is used to limit movement speed within the patient, for safety as an example. For example, in an embodiment of the invention, the maximum speed of the joystick movement of the medical instrument is 12 mm/s, the maximum angular movement of the medical instrument is 90°/s and/or the maximum speed of a balloon is 9.5 mm/s.

In an embodiment of the invention, control console assembly 102 is provided with an emergency stop button 308 which halts the medical procedure for example if there is a problem with the patient 104 and/or the devices 106 being used to treat the patient. Optionally, the emergency stop button 308 halts the medical procedure via controller 302 of control console 150, for example sending a command via control console 150 to devices 106 to stop and/or reverse what they are doing.

Control console assembly 102 is provided with radiation protection 316, in an embodiment of the invention. As described elsewhere herein, medical procedures are often performed in an environment which is hostile and/or harmful to an attending medical professional. In addition, the remedial measures taken to address this harmful operating environment are often themselves harmful to the professional. Therefore, in some embodiments of the invention, radiation protection 316 is integrated into control console assembly 102 in order to insulate the attending professional operating control console 150 from both the harmful operating environment and the harmful effects of conventional solutions to operating in the harmful environment. In an embodiment of the invention, radiation protection is included in the structure of control console assembly 102 (described in more detail with respect to FIG. 4), obviating the need for the professional to wear heavy insulating gear and/or a separate radiation protection structure. In some embodiments of the invention, a window 320 is provided to control console assembly 102 to allow the attending medical professional to have a line of sight to the patient 104. Optionally, window 320 also provides radiation protection. In an embodiment of the invention, window 320 is constructed from Kyowaglas-XA, manufactured by Kuraray Co. Ltd., Japan. This product is made of a shatter-resistant leaded plastic (lead acrylic sheet). Optionally, window 320 provides radiation protection equivalent to 0.5 mm thick of lead radiation shielding.

In an embodiment of the invention, remote control console assembly 102 is provided with mobility 318. As described above, remote is generally used to describe control console's 102 ability to maneuver independently of patient 104, medical imaging devices 108 and/or devices 106 for performing medical procedures, and therefore control console 102 is optionally at a remote location from patient 104, medical imaging devices 108 and/or devices 106 for performing medical procedures in the procedure room. Examples of this remote ability of the control console include: moving the control console to provide a maximum amount of radiation protection to the attending medical professional; moving the control console in order to have better visibility of the patient; moving the control console so that it does not interfere with the operation of medical imaging devices and/or medical instruments; and/or moving the control console from one room to another in order to allow the ability to perform procedures in more than one location using the same control console. Using wheels, tracks and/or something similar, control console assembly 102 can be positioned within an operating room at a location which the attending medical professional prefers in order to conduct the medical procedure. Optionally, mobility 318 provided to control console assembly 102 is motorized. In some embodiments of the invention, it is envisioned that control console assembly 102 is adapted for use in a plurality of locations whereby the same control console assembly 102 is usable to conduct procedures in different locations. Optionally, control console 150 is removably attached to control console assembly 102 and is interchangeable with other control console assemblies.

Figure 4:
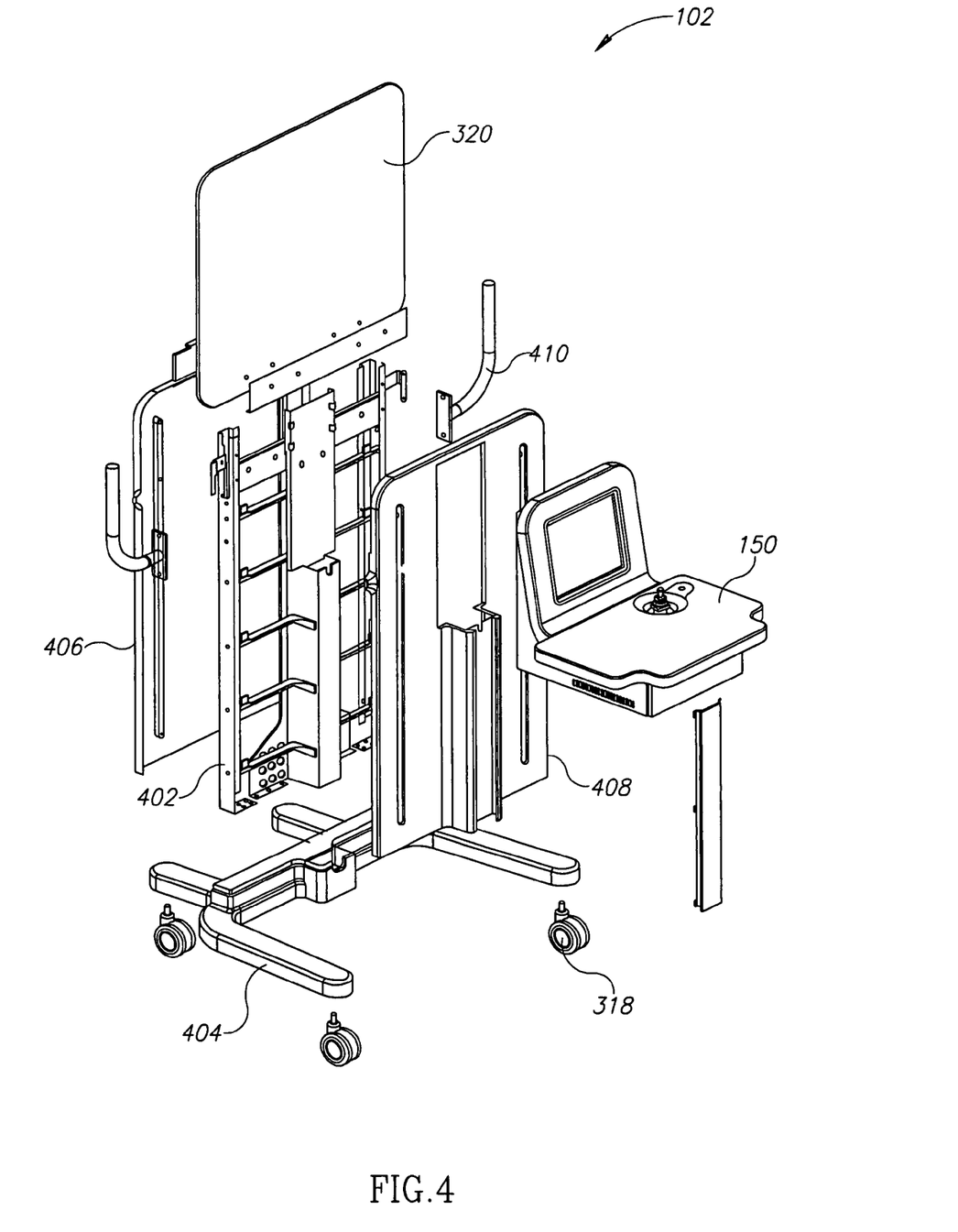
FIG. 4 is a perspective exploded view of a control console assembly, in accordance with an exemplary embodiment of the invention; and, FIG. 5 is a perspective exploded view of a control console, in accordance with an exemplary embodiment of the invention.

FIG. 4 is an exploded view of control console assembly 102, in accordance with an exemplary embodiment of the invention. It should be noted that control console 150 of FIG. 4 is not exploded since an exemplary control console 150 is depicted in an exploded view in FIG. 5 instead. In an embodiment of the invention, control console assembly 102 is provided with a central frame member 402 which is adapted to link many of the parts of control console assembly 102 together. Central frame member 402 is attached to a base 404, in some embodiments of the invention, which is adapted to mount a means for providing mobility 318, for example wheels and/or tracks, to control console assembly 102. In an embodiment of the invention, attached to central frame member 402 opposite from base 404 is window 320. Front 406 and back 408 cover plates are provided to central frame member 402 between base 404 and window 320, in some embodiments of the invention. Cover plates 406, 408 are used in some embodiments of the invention for providing radiation protection (for example, if constructed of a radiation non-transmissive material such as lead) and/or for providing an aesthetically pleasing appearance for control console assembly 102. Alternatively, additionally or optionally, radiation non-transmissive material is mounted on central frame member 402 directly with only some or no radiation protection coming from cover plates 406, 408. In some embodiments of the invention, at least 0.5 mm thick lead plate, or an equivalent, is used. In some embodiments of the invention, cover plates 406, 408 are adapted to accommodate other parts of control console assembly 102, such as being provided with an opening so that control console 150 can be affixed, optionally removably affixed, directly to central frame member 402. In some embodiments of the invention, at least one handle 410 is provided to control console assembly 102 for assisting with moving control console assembly 102 around. Optionally, at least one handle 410 is also adapted for mounting an output device 306, such as shown in FIG. 1 where a display is mounted on top of a handle.

In an embodiment of the invention, central frame member 402 is constructed of a material, such as metal, which can support the weight of the parts of control console assembly 102, such as control console 150, window 320, at least one handle 410, output device 306 and/or front 406 and/or back 408 cover plates.

It should be understood that the above described construction is by way of example only and that variations to the design and construction of control console assembly 102 would occur to those skilled in the art. For example, control console assembly 102 may not be provided with cover plates 406, 408, instead the central frame member 402 being provided with radiation protection and/or an aesthetic appearance. As another example of an alternative embodiment, central frame member 402 and base 404 are integrated, wherein a means for mobility 318 is attached to a unified central frame member/base. A still further example is a control console assembly where window 320 is incorporated within central frame member 402 rather than being affixed on one end of central frame member 402, as shown in FIG. 4.

Referring to FIGS. 1 and 4, a radiation shield comprises a front wall 408 and a window portion 320 being positioned between the display monitor 306 and the medical instrument 106. The front wall 408 is coplanar with a section of the window portion 320, and wherein the right and left lateral edges of the window portion extend laterally beyond left and right lateral edges of the front wall. First, second, third and fourth wheels 318 are attached to base 404. The front wall 408 includes a central point located equidistance from the left and right lateral edges of the front wall. The first wheel and second wheel are located in front of the front wall and the third wheel and the fourth wheel are located behind the front wall. The first wheel and third wheel are located on the left side of the central point and the second wheel and fourth wheel are located on the right side of the central point. The lateral distances from the central point to the first wheel and to the second wheel are less than the lateral distances from the central point to the third wheel and fourth wheel respectively. In one embodiment, a second display is connected to the control console and has a lateral edge located beyond one of the right and left lateral edges of the window such that one of the left and right lateral edges of the window portion is between the lateral edge of the second display and the first display.

FIG. 5 is an exploded view of control console 150, in accordance with an exemplary embodiment of the invention. A chassis 502 is provided to control console 150 to serve as a support base for components of control console 150. In an embodiment of the invention, chassis 502 is shielded to protect sensitive electrical components of control console 150 which are positioned within chassis 502, for example controller 302, data storage 310 and/or power supply 312. In some embodiments of the invention, at least one communication device 504 such as a hub or router adapted for enabling communication between control console 150 and other devices, described with respect to FIG. 2, is located within chassis 502. In an embodiment of the invention, chassis 502 is adapted to be removably affixed to the remainder of control console assembly 102 to allow detachable and/or interchangeable control consoles to be used with multiple control console assemblies.

In an embodiment of the invention, a top 506 is provided to control console 150 which sits on top of chassis 502 such that top 506 and chassis 502 are adapted to create an enclosed, or mostly enclosed, volume within control console 150. Controller 302, data storage 310 and/or power supply 312 are located within this volume, in some embodiments of the invention. Additionally, alternatively or optionally, top 506 also provides shielding to protect the area within control console 150. In some embodiments of the invention, access to the area within control console 150 is gained via a door 508 which is located at the front of control console 150. Top 506 is provided with at least one output device 306, such as a display, in an embodiment of the invention. Optionally, at least one output device is a touch screen display which also serves as an input device 304. Other input devices are optionally provided to control console 150, for example a joystick 510, a mouse 512 and/or a keyboard 514.

It should be understood that the above described construction is by way of example only and that variations to the design and construction of control console would occur to those skilled in the art. For example, joystick 510 (if present) may be placed somewhere other than on the upper surface 516 of top 506. Additionally or alternatively, keyboard 514 is integrated into upper surface 516. Optionally, control console 150 is not shaped as shown in FIG. 5, for example rather than being shaped like two nearly perpendicular components it is shaped like one upwardly angled or vertical component. In some embodiments of the invention, at least one of controller 302, data storage 310 and/or power supply 312 are located outside of control console 150, optionally positioned on some other portion of control console assembly 102.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". It should also be noted that the device is suitable for both males and female, with male pronouns being used for convenience. The scope of the invention is limited only by the following claims.

What is claimed:

1. An apparatus for control of a procedure, comprising:
a communications interface;
a control console separated from both an imaging device and a support for a patient on which the procedure is being performed, wherein the control console includes a first display monitor and is adapted to provide control commands via the communications interface to at least one medical instrument, the at least one medical instrument being a guide wire or a catheter used to perform the procedure;
at least one wheel coupled to the control console, wherein the at least one wheel is configured to contact a floor;

at least one radiation shield including a window portion attached to the control console, the window portion having left and right lateral edges, wherein the radiation shield including the window portion is positioned between the control console including the first display monitor and both the at least one imaging device and the entire patient, the window portion having a width greater than the width of the control console and first display monitor; and a second display connected to the control console and having a lateral edge located beyond one of the left and right lateral edges of the window portion, such that one of the left and right lateral edges of the window portion is between the lateral edge of the second display and the first display;

wherein the control console and the at least one radiation shield are fully supported by the at least one wheel;

wherein the at least one wheel allows the control console and at least one radiation shield to be freely translated together relative to the floor independent of the imaging device and the medical instrument to a plurality of operative positions distal from the imaging device and the patient, wherein the window portion of the radiation shield extends above the first display monitor;

wherein the control console comprises a joystick, wherein the joystick, when operated by the user, is configured to cause movement of the at least one medical instrument.

2. An apparatus according to claim 1, wherein the apparatus is adapted for remote control of the at least one medical instrument.

3. An apparatus according to claim 1, wherein the window portion of the radiation shield is adapted to allow a view of the patient when operating the control console.

4. An apparatus according to claim 1, wherein the control console is removably attached to the apparatus.

5. An apparatus according to claim 1, wherein the imaging device is an x-ray, a camera, ultrasound, CT or MRI imaging device.

6. An apparatus according to claim 1, wherein the at least one medical instrument is an ablation catheter, an EM mapping catheter, a pacing catheter, or a balloon catheter.

7. An apparatus according to claim 1, wherein the communications interface is adapted to provide communication between the control console and an information network.

8. An apparatus according to claim 1, wherein the communications interface is adapted to provide wireless communication from the control console to at least one of the at least one medical instrument used to perform the procedure and an information network.

9. An apparatus according to claim 1, wherein the control console comprises at least one output device and further wherein the at least one output device is a force feedback device.

10. An apparatus according to claim 1, further comprising a power supply.

11. An apparatus according to claim 1, further comprising an emergency stop button.

12. The apparatus of claim 1, wherein the lateral edges of the at least one radiation shield extend past the lateral edges of the control console.

13. The apparatus of claim 1, further comprising a central frame member, a front cover plate coupled to a front side of the central frame member, and a back cover plate coupled to a back side of the central frame member, wherein the front cover plate and the back cover plate are constructed of a radiation non-transmissive material, and further wherein the control console is coupled to and supported by the central frame member.

14. The apparatus of claim 13, wherein the window portion of the radiation shield is coupled to an upper end of the central frame member, the window portion of the radiation shield adapted to allow a view of the patient when operating the control console.

15. The apparatus of claim 14, further comprising a base coupled to a lower end of the central frame member, wherein the at least one wheel is coupled to the base.

16. The apparatus of claim 1, wherein the control console includes a chassis constructed of a radiation non-transmissive material to shield electrical components of the control console.

17. The apparatus for control of a procedure of claim 1, wherein a portion of the window portion of the radiation shield is positioned lower than a portion of the first display monitor.

18. The apparatus for control of a procedure of claim 1, wherein the window portion of the radiation shield is positioned relative to the first display monitor such that, when the control console and radiation shield are in one of the operative positions, there is a line of sight that extends above the first display monitor through the window portion of the radiation shield to the patient.

19. The apparatus for control of a procedure of claim 1, wherein the window portion of the radiation shield is positioned relative to the first display monitor such that, when the control console and radiation shield are in one of the operative positions, there is a vertical plane that is perpendicular to a surface of the window portion of the radiation shield that also intersects both the patient and a screen of the first display monitor.

20. The apparatus for control of a procedure of claim 1, further comprising a handle coupled to the radiation shield that may be grasped by a user to move the control console and the radiation shield between operative positions, wherein the radiation shield is non-convex relative to a user located at the control console.

21. The apparatus for control of a procedure of claim 19, wherein the handle extends beyond a lateral edge of the shield.

22. The apparatus for control of a procedure of claim 1, wherein the medical instrument is a catheter, and wherein the communications interface is adapted to provide a control signal to control a bedside system to extend and retract a catheter within a patient.

23. The apparatus for control of a procedure of claim 1, wherein the discrete movement comprises a discrete axial step and a discrete rotational increment.

24. The apparatus for control of a procedure of claim 23, wherein the control console is configured such that rotational movement of the joystick about a vertical axis of the joystick causes rotational movement of the at least one medical instrument.

25. The apparatus for control of a procedure of claim 1, wherein the radiation shield comprises a front wall and the window portion is coupled to and extends above the front wall, wherein the front wall is coplanar with a section of the window portion, and further wherein left and right lateral edges of the window portion extend laterally beyond left and right lateral edges of the front wall.

26. The apparatus for control of a procedure of claim 25, further comprising a handle coupled to the radiation shield that may be grasped by a user to move the control console and the radiation shield together between operative positions, wherein the handle extends beyond the lateral edges of both the front wall and the window portion of the radiation shield.

27. The apparatus for control of a procedure of claim 25, wherein the at least one wheel comprises:
   a first wheel;
   a second wheel;
   a third wheel;
   and a fourth wheel;
   wherein the front wall includes a central point located equidistance from the left and right lateral edges of the front wall;
   wherein the first wheel and the second wheel are located in front of the front wall and the third wheel and the fourth wheel are located behind the front wall;
   wherein the first wheel and the third wheel are located on the left side of the central point and the second wheel and fourth wheel are located on the right side of the central point; and
   wherein the lateral distances from the central point to the first wheel and to the second wheel are less than the lateral distances from the central point to the third wheel and the fourth wheel, respectively.

28. A medical device control system for remote control of a medical instrument, comprising:
   at least one medical instrument, the at least one medical instrument being a guide wire or a catheter;
   a control console assembly comprising:
      a communications interface providing control commands for the remote control of the medical instrument;
      a first display monitor;
      a second display monitor;
      a mobility element to allow the control console to be moved independently of the at least one medical instrument; and
      a radiation shield comprising a front wall and a window portion being positioned between the first display monitor and the at least one medical instrument, the window portion of the radiation shield being transparent and formed of a material substantially preventing radiation from being passed therethrough;
   wherein the front wall is coplanar with a section of the window portion, and further wherein left and right lateral edges of the window portion extend laterally beyond left and right lateral edges of the front wall, control console and first display monitor;
   wherein the second display monitor is connected to the control console and including a portion that extends beyond one of the left and right lateral edges of the window portion;
   wherein the mobility element allows both the control console and the shield to be freely positionable between a plurality of operative positions within an operating room distal from a patient on which a procedure is being performed.

29. The system according to claim 28, wherein the mobility element comprises a first wheel and a second wheel, wherein the first and second wheel are located on opposite sides of a plane defined by the radiation shield, and further wherein the first and second wheels are spaced apart from the plane defined by the radiation shield.

30. The system according to claim 28, wherein the at least one medical instrument is part of a bed side unit.

31. The system according to claim 28, further including panels operatively secured to the control console assembly to prevent radiation from passing therethrough, wherein the window portion has a bottom edge extending below an upper edge of the panels operatively secured to the control console assembly.

32. The system according to claim 28, wherein the first display monitor is adapted to display output from at least one imaging device employing radiation.

33. A method for the remote control of at least one medical instrument by a user for use in a medical procedure on a patient comprising:
   providing at least one remote controlled medical instrument proximate to the patient, the at least one remote controlled medical instrument being a guide wire or a catheter;
   providing a control console supported by a console assembly, the control console having a communication interface for sending signals to the remote controlled medical instrument, the control console assembly including a first display and a transparent shield being formed of a material preventing radiation from passing therethrough the transparent shield being supported by the console assembly, the transparent shield having a width greater than the width of the control console;
   providing a second display connected to the control console that is located beyond a lateral edge of the transparent shield;
   moving the control console assembly from a first position to a second position distal from the patient to allow an operator to view a patient through the shield, wherein the shield is positioned between the operator and the patient, wherein the control console assembly is freely positionable between a plurality of operative positions independent of an imaging system within an operating room;
   controlling the at least one medical instrument from behind the shield using the control console assembly in order to perform the medical procedure while the user's arms are completely behind the transparent shield;
   moving the control console assembly from the operating room to a second operating room; and
   controlling a second medical instrument from behind the shield in order to perform a second medical procedure on a second patient in the second operating room.

34. The method according to claim 33, the second operating room includes a second imaging system.

35. The method according to claim 33, further comprising providing a medical image to the control console formed with a radiation source.

* * * * *